United States Patent [19]

Ullmann et al.

[11] Patent Number: 5,348,675
[45] Date of Patent: Sep. 20, 1994

[54] HETEROPOLYSACCHARIDE BM07

[75] Inventors: Gabriel Ullmann, Ruffec; Alain Jarry, Poitiers, both of France

[73] Assignee: Rhone-Poulenc Chimie, Courbevoie Cedex, France

[21] Appl. No.: 5,572

[22] Filed: Jan. 19, 1993

Related U.S. Application Data

[62] Division of Ser. No. 379,478, Jul. 13, 1989, Pat. No. 5,252,727.

Foreign Application Priority Data

[30] Jul. 13, 1988 [FR] France ............... 88 09529

[51] Int. Cl.$^5$ ............ C07G 17/00; C12P 19/06; C12P 19/04; C11D 7/60
[52] U.S. Cl. .................... 252/82; 134/3; 134/41; 166/246; 166/295; 252/80; 252/87; 252/100; 252/136; 252/315.3; 435/101; 435/104; 435/252.1; 435/822; 536/114; 536/123; 536/124
[58] Field of Search ......... 435/101, 104, 252.1, 435/822; 536/114, 123, 124; 252/82, 80, 87, 100, 136, 315.3; 106/208; 134/3, 41; 166/246, 295

[56] References Cited

U.S. PATENT DOCUMENTS

| | | | |
|---|---|---|---|
| 3,960,832 | 6/1976 | Kang et al. | 536/123 |
| 4,269,939 | 5/1981 | Kang et al. | 435/104 |
| 4,339,239 | 7/1982 | Racciato | 435/104 |
| 4,634,667 | 1/1987 | Linton et al. | 435/104 |
| 4,689,160 | 8/1987 | Steenbergen et al. | 435/104 |
| 4,855,069 | 8/1989 | Schuppiser et al. | 252/82 |
| 4,873,323 | 10/1989 | Cros et al. | 536/114 |
| 4,898,819 | 2/1990 | Linossier | 435/104 |
| 4,941,533 | 7/1990 | Buller et al. | 166/246 |
| 5,010,186 | 4/1991 | Cros et al. | 536/114 |
| 5,017,479 | 5/1991 | Eyssautier | 435/101 |
| 5,236,046 | 8/1993 | Robison et al. | 166/246 |

FOREIGN PATENT DOCUMENTS 0040445 11/1981 European Pat. Off.

*Primary Examiner*—Herbert J. Lilling
*Attorney, Agent, or Firm*—Burns, Doane, Swecker & Mathis

[57] ABSTRACT

The novel heteropolysaccharide BM07, useful, e.g., as a thickening/stabilizing/suspending agent for a wide variety of industrial applications, is produced by fermenting a nutrient medium containing at least one source of assimilable carbon with a strain of *Agrobacterium tumefaciens* I-736, or recombinant or mutant thereof.

31 Claims, 2 Drawing Sheets

HETEROPOLYSACCHARIDE BM07

This application is a divisional, of application Ser. No. 07/379,478, filed Jul. 13, 1989 now U.S. Pat. No. 5,252,727.

BACKGROUND OF THE INVENTION

1. Field of the Invention

The present invention relates to a novel heteropolysaccharide, a process for the preparation thereof by microbial fermentation, and to the use of such novel heteropolysaccharide for a number of different applications.

2. Description of the Prior Art

Heteropolysaccharides (biopolymers) are known to this art as high molecular weight molecules containing at least two types of monosaccharides constituting a polymerized base unit.

One of the heteropolysaccharides most frequently used in industrial fields as varied as agricultural chemistry, agriculture, foodstuffs, the petroleum industry, cosmetics, etc., is xanthan gum.

However, in spite of its capabilities, xanthan gum has numerous shortcomings, notable among which is its lack of stability at elevated temperatures, in acid and alkaline media, and in strongly saline media.

Consequently, other heteropolysaccharides have come to be commercially available. Among the latter, the heteropolysaccharide developed by SHELL and marketed under the trademark SHELL-FLO S ® is representative. From analysis conducted on this product, it was determined that such heteropolysaccharide contains units derived from glucose, galactose and salts of pyruvic, succinic and acetic acids.

However, this heteropolysaccharide also has deficiencies, in particular when exposed to elevated temperatures on the order of 80° C.

SUMMARY OF THE INVENTION

Accordingly, a major object of the present invention is the provision of a novel heteropolysaccharide which is not only stable at elevated temperatures, but also in saline, basic or acid solutions, and which also exhibits strong rheological properties in low concentrations, high suspension capability, and rapid dissolution in both tap water and distilled water.

Another object of the present invention is the provision of a process for the preparation of such novel heteropolysaccharide.

Yet another object of this invention is the use of such novel heteropolysaccharide for a number of different applications.

Briefly, the present invention features a novel heteropolysaccharide BM07 that is produced by the fermentation of a medium containing at least one source of assimilable carbon, utilizing a culture of *Agrobacterium tumefaciens* I-736, one of its recombinants or one of its mutants.

DETAILED DESCRIPTION OF THE PREFERRED EMBODIMENTS OF THE INVENTION

Figure 1:
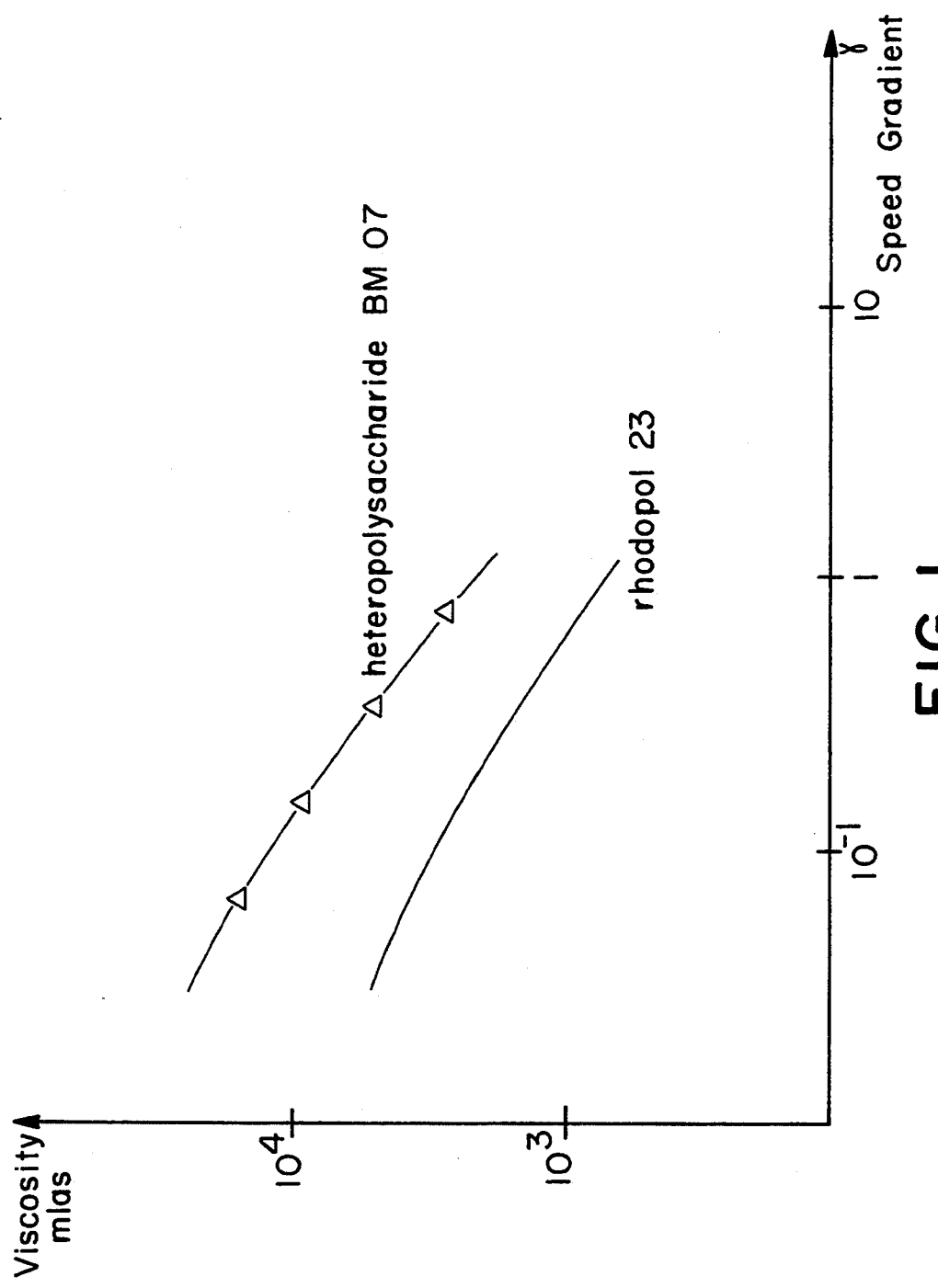
FIG. 1 is a graph plotting change in viscosity as a function of the velocity gradient, and comparing 0.1% by weight solutions, in distilled water, of the heteropolysaccharide BM07 of the invention versus xanthan gum.

More particularly according to the present invention, said strain of *Agrobacterium tumefaciens* I-736 has been deposited under the provisions of the Budapest Treaty with the National Collection of Cultures of Microorganisms (CNCM) on Mar. 1, 1988, and is accessible to the public under No. I-736. This strain originates from the National Collection of Phytopathogenic Bacteria and is recorded under No. CNBP 291 in the 1974 catalog of the organism curator.

A pure *Agrobacterium tumefaciens* I-736 culture may be prepared in an inclined (slanted) gelose tube incubated at a temperature of from 26° to 32° C. and more typically of from 28° to 32° C.

At these temperatures and in particular on media based on MY agar and Bennett agar, the compositions of which are indicated below, the formation of a mucoidal bacterial layer is observed which covers the totality of the slant in 20 hours.

The following support media were considered to be particularly advantageous for the culture of *Agrobacterium tumefaciens* I-736:

| MY agar medium (in g/l): | |
|---|---|
| Soy-peptones | 5 |
| Yeast extract | 3 |
| Malt extract | 3 |
| Glucose | 10 |
| Agar | 20 |
| T G Y agar medium (product of the Pasteur Institute) (in g/l): | |
| Peptones | 5 |
| Yeast extract | 2.5 |
| Glucose | 1 |
| Agar | 20 |
| Bennet Agar medium (in g/l): | |
| Peptone | 1 |
| Meat extract | 1 |
| NZ Amine A ® (product of the Sheffield Chemical Co.) | 2 |
| Glucose | 10 |
| Agar | 20 |
| T. S. Agar medium (product of the Bio-Merieux Co.) (in g/l): | |
| Bio trypease | 17 |
| Bio soyase | 3 |
| $K_2HPO_4$ | 2.5 |
| NaCl | 5 |
| Glucose | 2.5 |
| Agar | 20 |

The *Agrobacterium tumefaciens* I-736 strain may also be cultivated in a Petri dish, for example on a MY agar or TGY agar medium. Under these conditions, the colonies are visible within 24 to 30 hours and have the following characteristics, after 48 hours:

(i) Size: 2 to 3 mm in diameter;
(ii) Smooth or slightly bulging appearance;
(iii) Very clear brownish-yellow color; and
(iv) Colonies with clear edges and less mucoidal on the Petri dish than on the slant.

The *Agrobacterium tumefaciens* I-736 strain is able to utilize the following sugars:

(a) Glucose, (b) Saccharose,
(c) Starch hydrolysates, and more difficultly native starch and lactose.

Galactose and saccharose are the preferred sugars.

It has been determined that, in general, heteropolysaccharide BM07 contains units derived from glucose, galactose and pyruvic, succinic and acetic acids, or salts thereof, in the following respective proportions: 5-8/1-2/0.5-2/0.5-2/0.05-2, preferably 6-7.5/1-1.5/0-.5-1/0.5-1/0.05-0.2 and, even ore preferably, 7/1/0.5-1/0.5-1/0.05-0.1.

The said pyruvic, succinic and acetic acids are typically present in the form of their salts, such as sodium, potassium, calcium or ammonium salts.

The analytical methods used to determine the gross structure of the heteropolysaccharide BM07 entail the determination of the component elements (sugars and acids) after hydrolysis and chromatographic analysis by internal or external standardization.

Thus, the determination of the sugars is carried out in the following manner: 100 mg heteropolysaccharide BM07 are hydrolyzed in hermetically sealed tubes using 5 ml molar trifluoroacetic acid at 105° C. for 3 to 6 hours.

This operation is followed by evaporation to dryness and taking up the residue in 5 ml pyridine containing 15 mg sorbitol as the internal standard; then silylation of a 1 ml pyridine solution is carried out using 0.9 ml hexamethyldisilazane. The silylation if catalyzed by 0.1 ml trifluoroacetic acid.

The sugars are then analyzed by gaseous phase chromatography with F.I.D. detection on a capillary glass column 25 ml long and 0.25 mm in diameter, charged with a methylsilicone phase having a film diameter of $0.14\mu$. The gaseous vector is hydrogen, at a flow rate of 2 ml/min.

The amount of pyruvic acid is analyzed from a master solution obtained by the hydrolysis of 80 mg heteropolysaccharide BM07 using 5 ml 4N hydrochloric acid for 1 hour at 105° C., followed by the addition of 2 mg ketoglutaric acid (as the internal standard) and adjustment with 25 ml distilled water.

Analysis then is by High Performance Liquid Chromatography (HPLC) in a column packed with $C_{18}$ graft silica $5\mu$ in diameter, with the length of the column being 250 mm and its diameter 4.6 mm. The eluent used is a 50/50 mixture by volume of 0.02M phosphoric acid and acetonitrile. The flow rate is 1.5 ml/min.

Pyruvic acid is detected by ultraviolet light at 375 nm.

Succinic acid is determined following the hydrolysis of the heteropolysaccharide BM07 under the conditions used for pyruvic acid. The determination is direct, with external standardization. The standard succinic acid solution used contained 8 mg succinic acid in 25 ml water.

The HPLC technique is again used, on Aminex HPX87H® columns marketed by BIORAD. The eluent was 0.01N sulfuric acid and the flow rate was 0.8 ml/min. The detection of succinic acid is by refractometry.

The acetic acid is determined after the hydrolysis of 300 to 350 mg heteropolysaccharide BM07 using 5 ml 4N trifluoroacetic acid at 120° C. for 3 hours. 30 mg propionic acid are then added as the internal standard and determination is by gaseous phase chromatography with F.I.D. detection.

A 2 m long glass column is used for the analysis which has a 3 mm diameter, filled with a FFAP phase at 5% and 1% phosphoric acid absorbed on Chromosorb G ® (AW DMCS) with a 80 to 100 mesh. The vector gas is helium, at a flow rate of 30 ml/min.

The heteropolysaccharide BM07 emanating from different samples, has the following properties:

I. 1. The intrinsic viscosity ranges from 30 to 250 dl/g and more particularly from 140 to 250 dl/g, preferably from 150 to 240 dl/g.

The intrinsic viscosity ($\eta$) is determined by extrapolation at zero concentration of the reduced viscosity $(\eta-\eta_o)/\eta_o$ C, wherein:

(i) $\eta$ is the viscosity of the solution;
(ii) $\eta_o$ is the viscosity of the solvent; and
(iii) C is the heteropolysaccharide BM07 concentration, by using the Huggins equation:

$$\frac{\eta - \eta_o}{\eta_o C} = [n] + k' (n)^2 - C$$

$k'$ being the Huggins constant at the first Newtonian level.

The specific viscosity $(\eta-\eta_o)/\eta_o$ is measured as follows:

A master solution of 0.2 g/l heteropolysaccharide BM07 in an aqueous solution of 0.1M NaCl is prepared.

Next prepared is a range of solutions containing the heteropolysaccharide BM07 in concentrations of from 0.03 to 0.1 g/l by diluting the master solution with a 0.1M aqueous solution of NaCl.

The measurements were then carried out at 23° C. by means of a LOW SHEAR viscosimeter.

The curve of the specific viscosity is plotted as a function of the concentration and extrapolated to zero concentration.

2. The molecular weight of the heteropolysaccharide BM07 is measured by light diffusion and typically ranges from $6\times10^6$ to $10\times10^6$, preferably from $6.5\times10^6$ to $9.5\times10^6$.

II. Heteropolysaccharide BM07 has very good rheological properties in solution in distilled water, particularly at low concentrations. In addition, these properties are very well maintained when the heteropolysaccharide is exposed to severe conditions, in particular strongly acid or basic pH values, in strongly ionic media at elevated temperatures.

It will thus be seen that:

1. Solutions of 0.1% by weight of heteropolysaccharide BM07 in distilled water at 25° C. have viscosities after 24 hours greater than 350 mPa.s, notably ranging from 400 to 700 mPa.s; these viscosities are measured at a velocity gradient of 1 s$^{-1}$ using a LOW SHEAR viscosimeter.

2. The heteropolysaccharide BM07 has good rheological properties in a saline medium, and particularly in saline solutions based on $CaCl_2$, $Na_2SO_4$ and NaCl.

More particularly, it was found that 0.3% solutions by weight of heteropolysaccharide BM07 in a saline solution (composition given below) generally have viscosities after 2 hours ranging from 2,000 to 3,000 mPa.s and more particularly ranging from 2,500 to 3,000 mpa.s; these viscosities are measured using a Carrimed ® rheometer at a velocity gradient of 1 s$^{-1}$. The saline solution had the following composition:

| | |
|---|---|
| NaCl | 91.71 g |

| -continued | |
|---|---|
| CaCl$_2$.2H$_2$O | 10.41 g |
| MgCl$_2$.6H$_2$O | 10.12 g |
| BaCl$_2$.2H$_2$O | 0.113 g |
| NaHCO$_3$ | 0.195 g |
| Distilled water, qsp 1 l | |

On the other hand, 0.2% by weight solutions of heteropolysaccharide BM07 in 20% NaCl have viscosities, after 24 hours, ranging from 1,600 to 2,400 mPa.s and preferably ranging from 1,700 to 2,100 mPa.s; these viscosities are measured using a LOW SHEAR viscosimeter at a velocity gradient of 1 s$^{-1}$.

3. 0.2% by weight aqueous solutions of heteropolysaccharide BM07, at pH 1.7 and 25° C., after 24 hours, have a viscosity ranging from 1,000 to 2,500 mPa.s, more particularly ranging from 1,400 to 2,000 mPa.s; these viscosities are measured using a LOW SHEAR viscosimeter at a velocity gradient of 1 s$^{-1}$.

4. Aqueous 0.2% by weight solutions of heteropolysaccharide BM07 at pH 11.8 and 25° C., after 24 hours, have a viscosity ranging from 1,000 to 2,500 mPa.s, more particularly ranging from 1,400 to 2,000 mPa.s, measured using a LOW SHEAR viscosity meter at a velocity gradient of 1 s$^{-1}$.

5. 0.2% by weight heteropolysaccharide BM07 solutions in distilled water subjected to a temperature of 80° C. for 24 hours generally have viscosities ranging from 500 to 2,500 mPa.s and more particularly from 1,000 to 2,000 mPa; these viscosities are measured using a LOW SHEAR viscosimeter at a velocity gradient of 1 s$^{-1}$.

6. 0.2% by weight aqueous solutions of heteropolysaccharide BM07, at pH 7 and 25° C., after 24 hours, have a viscosity ranging from 1,000 to 2,500 mPa.s, more particularly ranging from 1,400 to 2,000 mPa.s, measured using a LOW SHEAR viscosimeter at a velocity gradient of 1 s$^{-1}$.

It has also been determined that heteropolysaccharide BM07 has good suspendability. The suspendability of solutions of heteropolysaccharide BM07 may be determined by the following test:

A 100 ml MRGAL test tube is filled completely (volume occupied 130 ml) with a 0.1% by weight solution of heteropolysaccharide BM07 in distilled water. The density of the solution is then about 1.

A sphere of polyamide 66, having a diameter of 3 mm and a density of 1.135 is placed on the surface of the liquid, without an initial velocity. The time of descent of the sphere is measured until it reaches the base of the test tube, i.e., after descending 23.5 cm. In order to obtain the mean time, the test is repeated several times. The mean dropping time is generally greater than 2,000 seconds and more particularly ranges from 3,000 to 15,000 seconds.

As a comparison, a 0.1% by weight solution of xanthan gum, under the same conditions, results in a time of descent of 60 to 350 seconds.

The present invention also features a process for the preparation of the heteropolysaccharide BM07 described above.

This process comprises the fermentation of a medium containing a source of assimilable carbon, using a strain of *Agrobacterium tumefaciens* I-736, or one of its recombinants or mutants.

In addition to said source of assimilable carbon, the fermentation medium may also contain a source of nitrogen, preferably organic nitrogen, and optionally one or more inorganic salts.

The medium is inoculated in conventional manner by the strain of *Agrobacterium tumefaciens* I-736.

If the volume of the fermentation medium is large, the inoculation may advantageously be carried out by means of an inoculation medium, seeded with a liquid preculture medium (the latter having been seeded beforehand with a pure culture of *Agrobacterium tumefaciens* I-736).

According to the process of the invention, any medium conventionally used for such purpose may be employed as the inoculation medium, advantageously a natural mineral medium. As the preculture medium, the medium YM bioth DIFCO Ref. 07101 is exemplary, and preferably a medium prepared from the following materials:

| (i) Soy - peptones | 5 g/l |
|---|---|
| (ii) Malt extract | 3 g/l |
| (iii) Yeast extract | 3 g/l |
| (iv) Glucose or saccharose | 10 g/l |

The natural pH of this medium ranges from 7 to 7.2 and is not adjusted.

As the organic source of carbon constituting the fermentation medium, sugars, such as glucose, saccharose, starch hydrolysates and optionally lactose or natural starch are exemplary, together with mixtures of these sugars. Glucose and saccharose are the preferred sugars. The concentration of the organic carbon source in the fermentation medium may range from 1 to 100 g/l and preferably from 15 to 60 g/l.

Exemplary organic source of nitrogen are casein and the caseinates, fish hydrolysates, wheat, corn or soy bean flour, yeast extracts (baker's yeast, beer yeast, lactic yeast, and the like), as are distiller's dry solubles, potato proteins, corn steap liquor (CSL) and the soluble fractions of CSL obtained by the dilution of CSL, followed by the elimination of solid particles by centrifugation, flushing or decantation. CSL and, in particular, the solubles from CSL, are especially preferred according to the invention.

The concentration of the organic source of nitrogen in the fermentation medium may range from 3 to 80 g/l, preferably from 5 to 50 g/l.

Exemplary inorganic salts that may optionally be incorporated into the fermentation medium are the sulfates, such as magnesium, manganese, zinc and iron sulfates, the carbonates, such as calcium carbonate, soluble calcium salts, and phosphates, such as potassium and sodium phosphate.

The concentration of each of these inorganic salts in the fermentation medium may range from 0.01 to 5 g/l, preferably from 0.05 to 2 g/l.

The fermentation medium may also contain oligoelements, such as trace amounts of salts of cobalt and/or molybdenum, together with vitamins and nucleotides.

The fermentation may be carried out at pressures of from 1 to 4 bar at a temperature of 25° C. to 35° C., preferably from 28° to 32° C., under submerged aerobic conditions.

The pH of the fermentation medium may range from 5 to 9 and preferably from 6 to 8. Their pH may be adjusted, depending on the particular circumstances, using a base such as sodium or potassium hydroxide, or with an acid, such as sulfuric, phosphoric, hydrochloric or nitric acid. The fermentation medium, placed, for example, into a tank or fermentation vessel, may advantageously be agitated.

The agitation may be carried out, for example, using a reciprocating or gyratory shaker, a mobile agitator or a bubble column. The fermentation time is usually longer than 30 hours, but generally ranges from 40 to 90 hours.

Fermentation yields are generally higher than 40%, more particularly range from 55% to 75% and even more particularly range from 60% to 75% by weight of heteropolysaccharide BM07 relative to the source of carbon used.

The heteropolysaccharide BM07 may then be separated from the fermentation medium.

For this, the fermentation wort containing the heteropolysaccharide BM07 may advantageously be heated to 80° to 120° C., for 10 to 60 min, and preferably from 15 to 45 min.

The wort subjected to this heat treatment advantageously has a pH of from 6 to 8.

However, this pH may be adjusted, if necessary, using a base or an acid.

The latter may be selected from among the aforementioned bases and acids used to adjust the pH of the fermentation medium.

The heteropolysaccharide may be recovered from the final wort of the fermentation by precipitation using an organic liquid miscible with water and in which the heteropolysaccharide is insoluble, or essentially insoluble.

Exemplary organic liquids useful for such purpose are acetone and alcohols, such as ethanol, propanol, isopropanol, butanol and tert-butanol.

Isopropanol is especially preferred according to the invention.

The volume of the organic liquid used is generally 2 to 3 times the volume of the wort to be treated.

The precipitation of the heteropolysaccharide by a liquid may also be carried out in the presence of salts, such as sodium, potassium or calcium sulfates, chlorides or phosphates.

The precipitated heteropolysaccharide BM07 may be separated from the organic liquid by filtration, centrifugation or draining.

The fibers obtained may be dehydrated, for example, with acetone or an alcohol, such as ethanol, propanol, isopropanol or tert-butanol.

The weight of the alcohol required for the dehydration operation is generally 1 to 10 times that of the fibers to be treated.

The dehydrated fibers may be subjected to repeated operations of filtration, centrifugation or draining.

The fibers may then be dried, ground and screened such as to provide a powder of heteropolysaccharide BM07. This powder usually is cream-beige in color.

In order to provide an even purer powder, it is possible to treat either the fermentation wort or an aqueous solution reconstituted from the resulting powder with one or more enzymes.

Exemplary enzymes suitable for this purpose are the proteases, mutanases, lipoproteases, cellulases and chitinases.

The enzymatic purification may be combined with or replaced by physical purification processes, such as the different techniques of filtration and dialysis, or by the various chromatography methods.

The fermentation worts or reconstituted aqueous solutions of heteropolysaccharide BM07, whether purified or not, may be concentrated. The concentration may be advantageous in certain cases, in particular to reduce transportation costs. Furthermore, concentrated solution may be applied more rapidly than the heteropolysaccharide powders. Concentration may be carried out by such methods as evaporation, ultrafiltration or difiltration.

Heteropolysaccharide BM07 is advantageously used in a number of different industrial fields wherein other water soluble polymers are already in use.

For these applications, heteropolysaccharide BM07 is principally employed as a thickening agent, suspension agent or as dispersion stabilizing agent, over a wide pH range, in the presence or absence of salts, nonionic or anionic surface active agents or other additives. In these applications, the amount of the heteropolysaccharide BM07 which is typically incorporated generally ranges from 0.001% to 2%, by weight, preferably from 0.1% to 1% by weight, based on the weight of the formulation comprised thereof.

Thus, heteropolysaccharide BM07 may be used:

(a) in the petroleum industry, for example in drilling fluids, in the assisted recovery of oil, in compositions used to fracture subterranean formations and compositions for treating wells;

(b) in ceramic compositions;

(c) in the food industry, in particular as a suspension or thickening agent;

(d) in paints, adhesives, inks;

(e) in cosmetics, in particular in shampoos, creams, lotions and toothpastes;

(f) in agrochemical compositions, in particular in "flowables" as a suspension agent;

(g) in the paper industry, particularly for coating papers;

(h) in lubricants;

(i) in industrial cleaners, for the treatment of metal surfaces;

(j) as agents for stabilizing various aqueous dispersions, such as micronized charcoal dispersions;

(k) in the textile industry, in particular in pastes for the printing of patterns;

(l) in the explosives industry;

(m) for the preparation of concretes and plasters, in particular in light of their coloration;

(n) in household or industrial cleaners, in particular as thickening agents or to stabilize abrasive particles.

In particular, heteropolysaccharide BM07 may be used as a thickener for aqueous acid compositions containing an organic or inorganic acid. Exemplary such organic acids are monocarboxylic acids, such as formic, acetic, chloroacetic, lactic, ascorbic and tannic acids, dicarboxylic acids, such as fumaric, malonic, succinic, glutaric, itaconic and tartaric acids, and tricarboxylic acids, such as citric acid.

Representative inorganic acids are hydrochloric acid, phosphoric acid, nitric acid and sulfuric acid.

All of the acids may be used either alone or as admixtures thereof. The relative proportions of the acid and the heteropolysaccharide may vary, in large measure as a function of such factors as the nature of each of the compounds, the viscosity desired and the specific application intended.

Generally, from 1% to 40% of the acid, 0.001% to 2% of the heteropolysaccharide and 55% to 98.99% water, are used.

Amounts of the heteropolysaccharide BM07 ranging from 0.1% to 1% are, however, preferred.

The compositions may be prepared in any desired manner, by mixing together the different components in water. It is preferable to initially dissolve the heteropolysaccharide in water, then add the acid or acids.

The compositions may also contain several other ingredients used in acid formulations, such as surface active agents, colorants, detergents, perfumes, bactericides and abrasives.

The subject compositions are more specifically useful for the cleaning of surface, the descaling of metal and porcelain surfaces and the descaling of metals.

In order to further illustrate the present invention and the advantages thereof, the following specific examples are given, it being understood that same are intended only as illustrative and in nowise limitative.

EXAMPLE 1

Process for the preparation of heteropolysaccharide BM07 on a mineral production medium:

A medium having the following composition (in g/l) was fermented by a strain of *Agrobacterium tumefaciens* I-736:

| | | |
|---|---|---|
| (i) | CSL (corn steap liquor) | 11 |
| (ii) | $MgSO_4.7H_2O$ | 0.5 |
| (iii) | $K_2HPO_4$ | 4 |
| (iv) | Saccharose | 25 |
| (v) | Potable water, qsp | 1 l |

The medium were fermented by said strain at a temperature of 28° C. under the following conditions:

(a) Fermentation in a 500 ml Erlenmeyer flask, having a useful volume of 100 ml.

This medium was subjected to agitation at 220 rpm by means of a gyratory shaker at an amplitude of 5 cm.

(b) Permentation in a 10 l tank having a useful volume of 6 l.

The medium was agitated at 270 rpm provided by means of notched square blades.

The medium was aerated with a stream of air at a rate of 500 l/h.

Fermentation in a 20 l BIOLAFFITE ® tank having a useful volume of 15 liters.

The medium was agitated at 400 rpm, provided by a RUSHTON ® type agitator.

The medium was aerated in a stream of air at a rate of 825 l/h.

The results obtained are reported in TABLE I:

TABLE I

| | End of Fermentation | Yield | Viscosity |
|---|---|---|---|
| Erlenmeyer flask | 80 h | 72% | 6,400 mPa.s |
| 10 Liter tank | 100 h | 67% | 9,000 mPa.s |
| 20 Liter tank | 90 h | 66% | 6,800 mpa.s |

In Table I, the "end of fermentation" corresponds to the total or quasi-total consumption of saccharose and the yield corresponds to the ratio in % of the weight of the heteropolysaccharide BM07 and the weight of the saccharose used.

The viscosity was that of the wort at the end of fermentation, measured by means of a Brookfield LVT ® viscosimeter fitted with a cylindrical needle 4, at 30 rpm.

EXAMPLE 2

Recovery of the heteropolysaccharide BM07 from the fermentation wort

The recovery of the heteropolysaccharide was from 2 kg of the wort produced by the fermentation of an organic production medium, contained in a 20 l tank, according to Example 1.

The wort was heat treated at 90° C. for 30 min.

To the wort thus treated, 2,300 ml isopropyl alcohol (IPA) were added. Precipitation was carried out in the presence of 150 g sodium sulfate.

The fibers resulting from the precipitation were then dehydrated twice in the presence of 1,200 ml IPA.

The fibers were then drained, disintegrated and dried in an oven at 85° C.

The dried material was then ground and screened.

A cream-colored powder of the heteropolysaccharide BM07 was obtained.

EXAMPLE 3

Rheological properties of heteropolysaccharide BM07 in distilled water at pH 7

The viscosity and the flow threshold of solutions in distilled water at pH 7 of heteropolysaccharide BM07, at different concentrations, were measured.

The tests were carried out using the powder of heteropolysaccharide BM07 as prepared in Example 2.

Solutions with 0.2% and 0.3% by weight of heteropolysaccharide BM07 were prepared by the addition of distilled water to said powder, followed by agitation using a Rayneri ® type agitator operating at 1,000 to 1,200 rpm for 15 min. The dissolution in the distilled water was complete after 15 min.

0.1% by weight solutions of the heteropolysaccharide were produced by simple dissolution of the above 0.2% solutions in distilled water.

The tests were carried out at 25° C., 24 h after the preparation of the solutions.

Comparative tests were carried out under the same conditions using RHODOPOL 23 ® (xanthan gum marketed by RHONE-POULENC).

Values of the flow threshold and viscosity of tests 1 to 4 were carried out using a LOW SHEAR viscosimeter, and a RHEOMAT 30 for the measurements of Tests 5 and 6.

The results obtained are reported in Table II:

TABLE II

Rheological properties of heteropolysaccharide BM07 and Rhodopol 23 ® in solution in distilled water at different concentrations:

| Test | Concentration in heteropolysaccharide | Flow threshold (in mPa) | Viscosity in mPa.s at shearing velocities of: | | |
|---|---|---|---|---|---|
| | | | $0.03\ s^{-1}$ | $0.1\ s^{-1}$ | $1\ s^{-1}$ |
| 1 | Heteropolysaccharide BM07, 0.1% Solution | 172 | 5,020 | 2,800 | 600 |
| 2 | Rhodopol 23 ®, 0.1% Solution | 22 | 810 | 510 | 200 |
| 3 | Heteropolysaccharide BM07, 0.2% Solution | 870 | 24,145 | 12,000 | 2,200 |
| | Rhodopol 23 ®, 0.2% Solution | 170 | 5,200 | 3,050 | 700 |
| 5 | Heteropolysaccharide BM07, 0.3% Solution | 3,155 | | 28,000 | 3,800 |
| 6 | Rhodopol 23 ®, 0.3% Solution | 930 | | 8,500 | 1,450 |

This table clearly shows that heteropolysaccharide BM07 in solution in distilled water is more pseudoplastic than xanthan gum under the same conditions.

A 0.1% by weight solution of the heteropolysaccharide had the same properties as a 0.2% xanthan gum solution.

Figure 2:
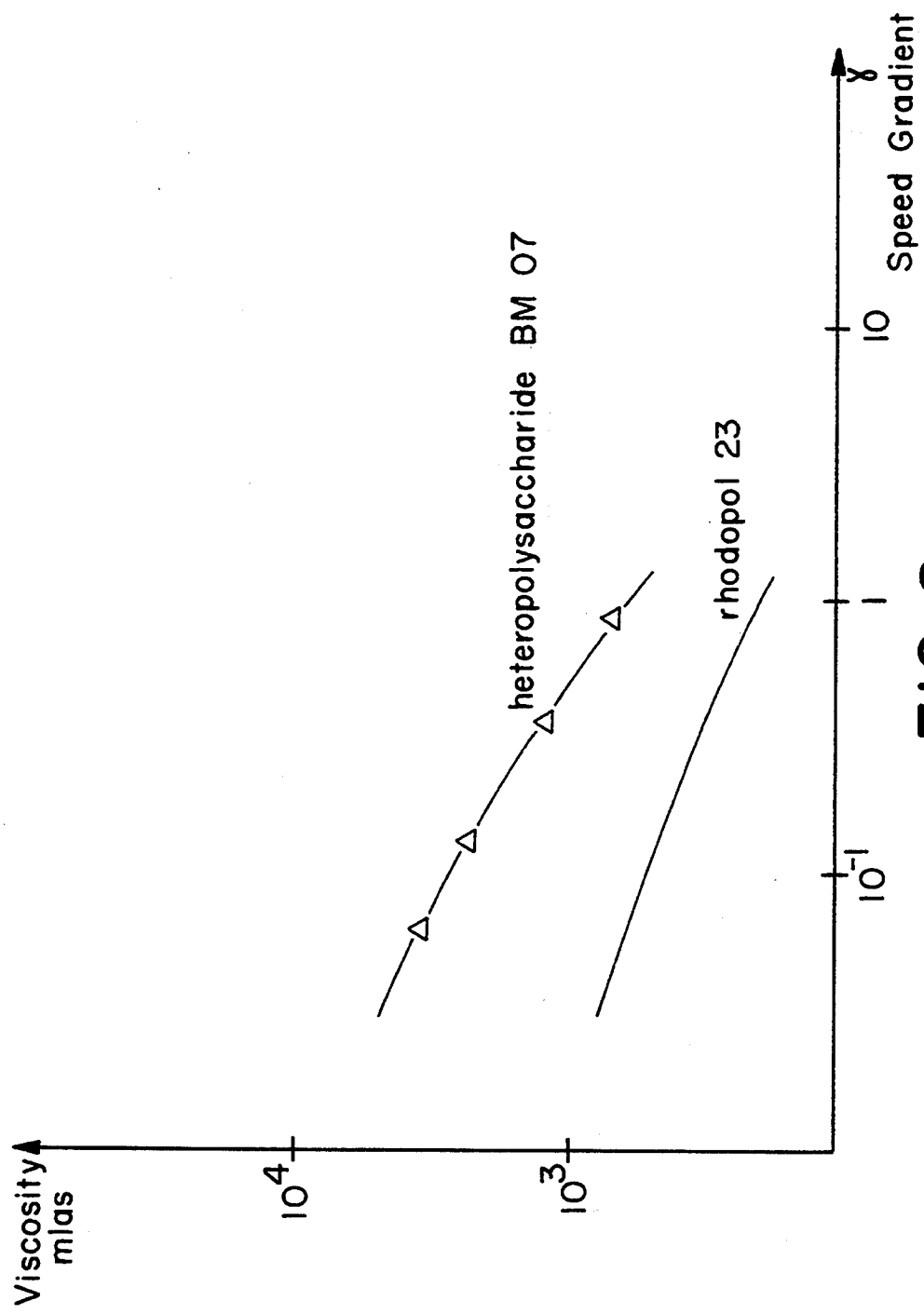
FIG. 2 is also a graph plotting change in viscosity as a function of the velocity gradient, this time comparing 0.2% by weight solutions, in distilled water, of the heteropolysaccharide BM07 of the invention versus xanthan gum.

FIGS. 1 and 2 illustrate the change in viscosity as a function of the velocity gradient, of solutions in distilled water of, respectively, 0.1% and 0.2% by weight heteropolysaccharide BM07 and xanthan gum (RHODOPOL 23 ®). The viscosity measurements were carried under the aforedescribed conditions.

EXAMPLE 4

Rheological properties of heteropolysaccharide BM07 in tap water at pH 7 at 22° HT Tests were carried out using 0.1% and 0.2% solutions by weight of heteropolysaccharide BM07 in tap water at pH 7, under the conditions of Example 3.

It was noted, however, that the dissolution of the heteropolysaccharide BM07 was easier in distilled water than in tap water.

The results of the tests, together with those of comparative tests carried out under the same conditions but using RHODOPOL 23 ®, are reported in Table III below.

Viscosities and flow thresholds were measured using a LOW SHEAR viscosimeter in Tests 7 and 9 and a RHEOMAT 30 in Test 8.

TABLE III

| Test | Concentration in heteropolysaccharide | Flow threshold (in mPa) | Viscosity in mPa.s at shearing velocities of: | | |
|---|---|---|---|---|---|
| | | | $0.03\ s^{-1}$ | $0.1\ s^{-1}$ | $1\ s^{-1}$ |
| 7 | Heteropolysaccharide BM07, 0.1% Solution | 130 | 3,750 | 1,975 | 430 |
| 8 | Rhodopol 23 ®, 0.1% Solution | 54 | — | — | 95 |
| 9 | Heteropolysaccharide BM07, 0.2% Solution | 850 | 22,940 | 10.500 | 1,750 |

EXAMPLE 5

Effect of pH, temperature and shearing rate on the rheological properties of heteropolysaccharide BM07

The effect of pH on the rheological properties of heteropolysaccharide BM07 was determined on 0.2% by weight solutions of said heteropolysaccharide BM07 as described in Example 3, but at a pH of 1.7 (after the addition of a sufficient amount of formic acid) and at pH 11.8 (after the addition of a sufficient amount of sodium hydroxide).

The tests were carried out at 22° C., 24 hours, 7 days and 1 month after the preparation of the solutions.

The influence of temperature was determined on 0.2% by weight solutions of heteropolysaccharide BM07, as described in Example 3.

The measurements were carried out using solutions subjected to a temperature of 80° C. for 1 hour and 24 hours.

To determine the effect of shearing on 0.2% solutions of heteropolysaccharide BM07, as described in Example 4, the solutions were subjected to shearing by an ULTRA TURRAX JANKE-KUNKEL TP 18–20 apparatus at a maximum velocity of about 2,000 rpm for 5 min, immediately following the preparations of the solutions. The measurements were carried out 24 hours after this operation.

Comparative tests were carried out using 0.2% solutions of RHODOPOL 23 ® treated under the same conditions.

A LOW SHEAR viscosimeter was used for the measurements.

The results are reported in Table IV.

It will be seen that the maintenance of the rheological properties of heteropolysaccharide BM07, in particular under the influence of an acid or basic pH, was very good and completely comparable to the behavior in distilled water, in particular over a time period of 1 month.

TABLE IV

Rheological properties of heteropolysaccharide BM07 under the influence of pH, temperature and shear rate and comparison with RHODOPOL 23 ® under the same conditions:

| Test | Conditions under which the 0.2% solutions of BM07 and Rh 23 were tested | Time | Flow threshold (in mPa) | Viscosity at the following shear rates (in mPa.s): | | |
|---|---|---|---|---|---|---|
| | | | | $0.03\ s^{-1}$ | $0.1\ s^{-1}$ | $1\ s^{-1}$ |
| 10 | BM07 at pH 1.7 | 24 hours | 720 | 19,300 | 8,750 | 1,550 |
| | | 7 days | 760 | 20,485 | 9,000 | 1,600 |
| | | 1 month | 830 | 22,250 | 11,000 | 1,600 |
| 11 | Rh 23 at pH 1.7 | 24 hours | 30 | | 670 | 295 |
| 12 | BM07 at pH 11.8 | 24 hours | 830 | 22,530 | 10,500 | 1,800 |
| | | 7 days | 900 | 24,370 | 11,000 | 1,900 |
| | | 1 month | 1,080 | 28,940 | 13,500 | 2,100 |
| 13 | Rh 23 at pH 11.8 | | 100 | 1,850 | | 540 |
| 14 | BM07, temperature of 80° C. | 1 hour | 592 | | 8,500 | 1,700 |
| | | 24 hours | 471 | | 7,000 | 1,400 |
| 15 | Rh 23, temperature of 80° C. | 1 hour | 58 | | 1,300 | 500 |
| | | 24 hours | 27 | | 800 | 370 |
| 16 | BM07 - ULTRA TURRAX | 24 hours | 711 | | 10,000 | 2,000 |
| 17 | Rh 23 - ULTRA TURRAX | 24 hours | 15 | | 580 | 315 |

In this table: BM07 is heteropolysaccharide BM07 and Rh 23 is RHODOPOL 23
(measurements carried out using a low-shear viscosimeter)

EXAMPLE 6

Effect of a strongly ionic medium on the rheological properties of heteropolysaccharide BM07

Tests 18 to 23 were carried out using 0.2% solutions of heteropolysaccharide BM07 containing 20% NaCl.

These solutions were prepared from a master solution in distilled water of heteropolysaccharide BM07 as prepared in Example 2; the master solution was diluted with a NaCl solution until the desired concentrations in heteropolysaccharide BM07 and NaCl were obtained.

The tests were carried out under the same conditions using 0.2% solutions of RHODOPOL 23 ® obtained by the same process. Viscosity and flow threshold measurements were carried out using a LOW SHEAR viscosimeter.

The results are reported in Table V which follows:

TABLE V

Rheological properties of heteropolysaccharide BM07 and RHODOPOL 23 ® in a 20% NaCl solution:

| Test | Product | Time | Flow threshold (in mPa) | Viscosity in mPa.s at the following shear rates: | | |
|---|---|---|---|---|---|---|
| | | | | $0.03\ s^{-1}$ | $0.1\ s^{-1}$ | $1\ s^{-1}$ |
| 18 | heteropolysaccharide BM07 | 24 hours | 913 | 24,535 | 11,500 | 1,800 |
| 19 | | 7 days | 968 | 26,100 | 12,000 | 2,000 |
| 20 | | 1 month | 923 | 25,150 | 12,000 | 3,000 |
| 21 | RHODOPOL 23 ® | 24 hours | 285 | 8,255 | 4,200 | 950 |
| 22 | | 7 days | 252 | 7,305 | 3,900 | 900 |
| 23 | | 1 month | 281 | 8,105 | 4,200 | 950 |

Tests 24 to 26 and 27 to 29 were carried out using 0.3% by weight solutions of heteropolysaccharide BM07 prepared as in Example 3, by the addition of the heteropolysaccharide to distilled water containing 10% by weight $Na_2SO_4$ or NaCl. The tests were carried out 4 hours, 7 days and 1 month after the preparation of the solutions, maintained in the case of Tests 24 to 26 at 22° C. and in the case of Tests 27 to 29 at 40° C. Viscosity measurements were carried out using a BROOKFIELD L.V.T. rheometer at 60 rpm.

The results of Tests 24 to 26 and 27 to 29 are reported in Tables VI and VII below:

TABLE VI

Rheological properties of heteropolysaccharide BM07 in 10% saline solutions at 22° C.:

| Test | Nature of salt | Viscosity in mPa.s after: | | |
|---|---|---|---|---|
| | | 4 hours | 7 days | 1 month |
| 24 | $CaCl_2$ | 530 | 650 | 640 |
| 25 | $Na_2SO_4$ | 560 | 680 | 640 |
| 26 | NaCl | 500 | 620 | 580 |

TABLE VII

Rheological properties of heteropolysaccharide BM07 in 10% saline solutions at 40° C.:

| Test | Nature of salt | Viscosity in mPa.s after: | | |
|---|---|---|---|---|
| | | 4 hours | 7 days | 1 month |
| 27 | $CaCl_2$ | 550 | 610 | 630 |
| 28 | $Na_2SO_4$ | 620 | 510 | 450 |
| 29 | NaCl | 590 | 460 | |

EXAMPLE 7

The following tests 30 and 31 evidence the good maintenance at elevated temperature of heteropolysaccharide BM07 solutions compared to solutions of SHELL-FLO S ®.

0.3% by weight solutions of heteropolysaccharide BM07 in distilled water were prepared under the conditions of Example 3.

0.3% solutions of SHELL-FLO S ® were prepared in the same manner.

These solutions were subjected to a temperature of 80° C. for 30 min. After 2 hours at rest, the viscosities and flow thresholds were measured using a Carrimed CS 50 rheometer.

The results are reported in Table VIII which follows:

TABLE VIII

| Test | 0.3% solution of | Flow threshold (in mPa) | Viscosity (mPa.s) at $1\ s^{-1}$ |
|---|---|---|---|
| 30 | heteropolysaccharide BM07 | 1,080 | 2,415 |
| 31 | SHELL FLO S ® | 66 | 323 |

EXAMPLE 6

Use of heteropolysaccharide BM07 in descaling compositions:

A descaling composition was prepared by introducing into a flask:

| (i) Heteropolysaccharide BM07 | 0.25% |
|---|---|
| (ii) Water | 87.70% |
| (iii) Formic acid | 10% |
| (iv) Ethoxynonylphenol (12 OE) | 2% |
| (v) Perfume and colorant | 0.05% |

The pH of the composition was 1.4.

The stability of the composition was evaluated as a function of temperature and storage time, by measuring the viscosity with a Rheomat 30 over a wide range of velocity gradients ($0.1\ s^{-1}$ to $100\ s^{-1}$) and a Brookfield LVT viscosimeter at 20 rpm.

The measurements were carried out at 20° C. and the results are reported in Table IX which follows:

TABLE IX

| Test | Temperature (°C.) | Viscosity in mPa.s measured on a Rheomat 30 Velocity gradient | | | | Viscosity in mPa.s measured on a Brookfield LVT viscosimeter at 30 rpm |
|---|---|---|---|---|---|---|
| | | $0.1\ s^{-1}$ | $1\ s^{-1}$ | $10\ s^{-1}$ | $100\ s^{-1}$ | |
| 2 hours | 20 | 12,500 | 2,000 | 300 | 48 | 505 |
| 8 days | 20 | 13,000 | 1,950 | 295 | 46 | 560 |
| 1 day | 40 | 13,500 | 2,000 | 295 | 46 | 560 |
| 8 days | 40 | 13,000 | 1,950 | 295 | 45 | 555 |

SHELL-FLO S ® is a heteropolysaccharide developed by SHELL containing units derived from glucose, galactose and salts of pyruvic, acetic and succinic acids.

While the invention has been described in terms of various preferred embodiments, the skilled artisan will appreciate that various modifications, substitutions, omissions, and changes may be made without departing from the spirit thereof. Accordingly, it is intended that

What is claimed is:

1. A process for the preparation of heteropolysaccharide BM07, comprising fermenting a nutrient medium containing at least one source of assimilable carbon by a strain of *Agrobacterium tumefaciens* I-736, or one of the mutants thereof and recovering said heteropolysaccharide BM07 from said medium.

2. The process as defined by claim 1, said at least one source of assimilable carbon comprising glucose, saccharose or a starch hydrolysate.

3. The process as defined by claim 1, wherein the concentration of the at least one source of assimilable carbon in the fermentation medium ranges from 1 to 100 g/l.

4. The process as defined by claim 1, said fermentation medium comprising at least one source of organic nitrogen.

5. The process as defined by claim 4, said at least one source of organic nitrogen comprising casein, a caseinate, wheat, corn or soybean flour, a yeast extract, a dry distiller's soluble, potato protein, corn steep liquor or solubles of corn steep liquor.

6. The process as defined by claim 5, said at least one source of organic nitrogen comprising corn steep liquor or soluble of corn steep liquor.

7. The process as defined by claim 4, wherein the concentration of the at least one source of organic nitrogen in the fermentation medium ranges from 3 to 80 g/l.

8. The process as defined by claim 1, said fermentation medium comprising at least one inorganic salt.

9. The process as defined by claim 8, said at least one inorganic salt comprising a sulfate or a carbonate.

10. The process as defined by claim 8, wherein the concentration of said at least one inorganic salt ranges from 0.01 to 5 g/l.

11. The process as defined by claim 1, carried out at a pressure ranging from 1 to 4 bar and at a temperature ranging from 25° C. to 35° C., under submerged aerobic conditions.

12. The process as defined by claim 1, wherein the pH of the fermentation medium ranges from 5 and 9.

13. The process as defined by claim 1, wherein the fermentation yield ranges from 40% to 75% by weight of the heteropolysaccharide BM07 relative to the at least one carbon source.

14. The process as defined by claim 1, comprising separating the heteropolysaccharide BM07 from the fermentation wort by (a) heating the wort to 80° to 120° C. for 10 to 60 min, (b) precipitating the heteropolysaccharide BM07 with an organic liquid that is miscible with water, and (c) separating the heteropolysaccharide BM07 from the organic liquid by filtration, centrifugation or draining.

15. The process as defined by claim 14, said organic liquid comprising ethanol, propanol, isopropanol, butanol or tert-butanol.

16. The process as defined by claim 14, further comprising dehydrating, drying, grinding and classifying said separated heteropolysaccharide BM07.

17. A thickening agent comprising the heteropolysaccharide BM07 produced by fermentation of a medium comprising at least one source of assimilable carbon, by a strain of *Agrobacterium tumefaciens* I-736, or one of the recombinants or mutants thereof.

18. A suspending agent comprising the heteropolysaccharide BM07 produced by fermentation of a medium comprising at least one source of assimilable carbon, by a strain of *Agrobacterium tumefaciens* I-736, or one of the recombinants or mutants thereof.

19. A stabilizing agent comprising the heteropolysaccharide BM07 produced by fermentation of a medium comprising at least one source of assimilable carbon, by a strain of *Agrobacterium tumefaciens* I-736, or one of the recombinants or mutants thereof.

20. A composition of matter comprising an aqueous solution of an organic acid, strong base and/or salt of an organic or inorganic acid, said aqueous solution containing a thickening amount of the heteropolysaccharide BM07 produced by fermentation of a medium comprising at least one source of assimilable carbon, by a strain of *Agrobacterium tumefaciens* I-736, or one of the recombinants or mutants thereof.

21. In a process for the thickening of an aqueous medium, the improvement which comprises utilizing as the thickening agent therefor, an effective amount of the heteropolysaccharide BM07 produced by fermentation of a medium comprising at least one source of assimilable carbon, by a strain of *Agrobacterium tumefaciens* I-736, or one of the recombinants or mutants thereof.

22. In a process for the cleaning or descaling of a substrate surface, the improvement which comprises including in the cleaning/descaling composition therefor, the heteropolysaccharide BM07 produced by fermentation of a medium comprising at least one source of assimilable carbon, by a strain of *Agrobacterium tumefaciens* I-736, or one of the recombinants or mutants thereof.

23. The heteropolysaccharide BM07 produced by fermentation of a medium comprising at least one source of assimilable carbon, by a strain of *Agrobacterium tumefaciens* I-736, or one of the recombinants or mutants thereof, having an intrinsic viscosity ranging from 140 to 250 dl/g.

24. The heteropolysaccharide BM07 as defined by claim 23, having an intrinsic viscosity ranging from 150 to 240 dl/g.

25. A solution comprising (i) 0.1% by weight of a heteropolysaccharide BM07 produced by fermentation of a medium comprising at least one source of assimilable carbon by a strain of *Agrobacterium tumefaciens* I-756, or one of the recombinants or mutants thereof, and (ii) distilled water, said solution having a viscosity at 25° C. after 24 hours ranging from 400 to 700 mPa.s.

26. A solution comprising (i) 0.2% by weight of a heteropolysaccharide BM07 produced by fermentation of a medium comprising at least one source of assimilable carbon by a strain of *Agrobacterium tumefaciens* I-736, or one of the recombinants or mutants thereof, and (ii) a 20% aqueous solution of NaCl, said solution having a viscosity after 24 hours ranging from 1,700 to 2,100 mPa.s.

27. An aqueous solution comprising 0.2% by weight of a heteropolysaccharide BM07 produced by fermentation of a medium comprising at least one source of assimilable carbon, by a strain of *Agrobacterium tumefaciens* I-736, or one of the recombinants or mutants thereof at pH, said solution having a viscosity at pH 7 and 25° C. ranging from 1,400 to 2,000 mPa.s.

28. An aqueous solution comprising 0.2% by weight of a heteropolysaccharide BM07 produced by fermentation of a medium comprising at least one source of assimilable carbon, by a strain of *Agrobacterium tumefaciens* I-736, or one of the recombinants or mutants thereof, said solution having a viscosity at pH 1.7 and 25° C. after 24 hours ranging from 1,400 to 2,000 mPa.s.

29. An aqueous solution comprising 0.2% by weight of a heteropolysaccharide BM07 produced by fermentation of a medium comprising at least one source of assimilable carbon, by a strain of *Agrobacterium tumefaciens* I-736, or one of the recombinants or mutants thereof, said solution having a viscosity at pH 11.8 and 25° C. after 24 hours ranging from 1,400 to 2,000 mPa.s.

30. A solution comprising (i) 0.2% by weight of a heteropolysaccharide BM07 produced by fermentation of a medium comprising at least one source of assimilable carbon by a strain of *Agrobacterium tumefaciens* I-736, or one of the recombinants or mutants thereof and (ii) distilled water, said solution being subjected to a temperature of 80° C. for 24 hours and having a viscosity ranging from 1,000 to 2,000 mPa.s.

31. The process as defined by claim 3, said concentration ranging from 15 to 60 g/l.

* * * * *